United States Patent [19]
Selman

[11] Patent Number: 5,336,224
[45] Date of Patent: Aug. 9, 1994

[54] BONE FIXATION PLATE

[75] Inventor: Corey M. Selman, Long Beach, Calif.

[73] Assignee: Ace Medical Company, Los Angeles, Calif.

[21] Appl. No.: 983,402

[22] Filed: Nov. 30, 1992

[51] Int. Cl.5 ............................................. A61B 17/58
[52] U.S. Cl. ................................................... 606/69
[58] Field of Search .................. 606/69, 71, 72, 60, 606/70; 623/16

[56] References Cited

U.S. PATENT DOCUMENTS

| | | | |
|---|---|---|---|
| 2,441,765 | 5/1948 | Hopkins | 129/92 |
| 2,494,229 | 7/1946 | Collison | 606/69 |
| 3,593,709 | 7/1971 | Halloran | 128/92 |
| 4,218,015 | 8/1980 | Steinemann | 128/92 D |
| 4,573,458 | 3/1986 | Lower | 606/69 |
| 4,743,260 | 5/1988 | Burton | 606/61 |
| 4,905,679 | 3/1990 | Morgan | 606/70 |
| 4,923,471 | 5/1990 | Morgan | 606/69 |
| 5,053,036 | 10/1991 | Perren et al. | 606/71 |
| 5,092,893 | 3/1992 | Smith | 606/60 |
| 5,151,103 | 9/1992 | Tepic et al. | 606/69 |

FOREIGN PATENT DOCUMENTS

| | | | |
|---|---|---|---|
| 0266146 | 5/1988 | European Pat. Off. | 606/69 |
| 0290138 | 11/1988 | European Pat. Off. | 606/69 |
| 2622431 | 5/1989 | France | 606/72 |

OTHER PUBLICATIONS

Zimmer, Fracture Appliances: Sherman Type S-MO Plates and Screws, Feb. 1, 1947.

Primary Examiner—David Isabella
Assistant Examiner—Debra S. Brittingham
Attorney, Agent, or Firm—Kinney & Lange

[57] ABSTRACT

An implantable bone plate comprises a solid, elongated, generally circular rod member having a plurality of axially-aligned flat members spaced apart along the length thereof. Each flat member has a width greater than the thickness of the rod member and an aperture for receiving a bone screw or the like. The apertures are normal to and intersect the axis of the rod member. The thickness of the flat members is preferably at least as great as the thickness of the rod member so that only the flat members bear against a bone. Preferably, the flat members are truncated spherical members whose spherical surfaces intersect the rod member.

18 Claims, 2 Drawing Sheets

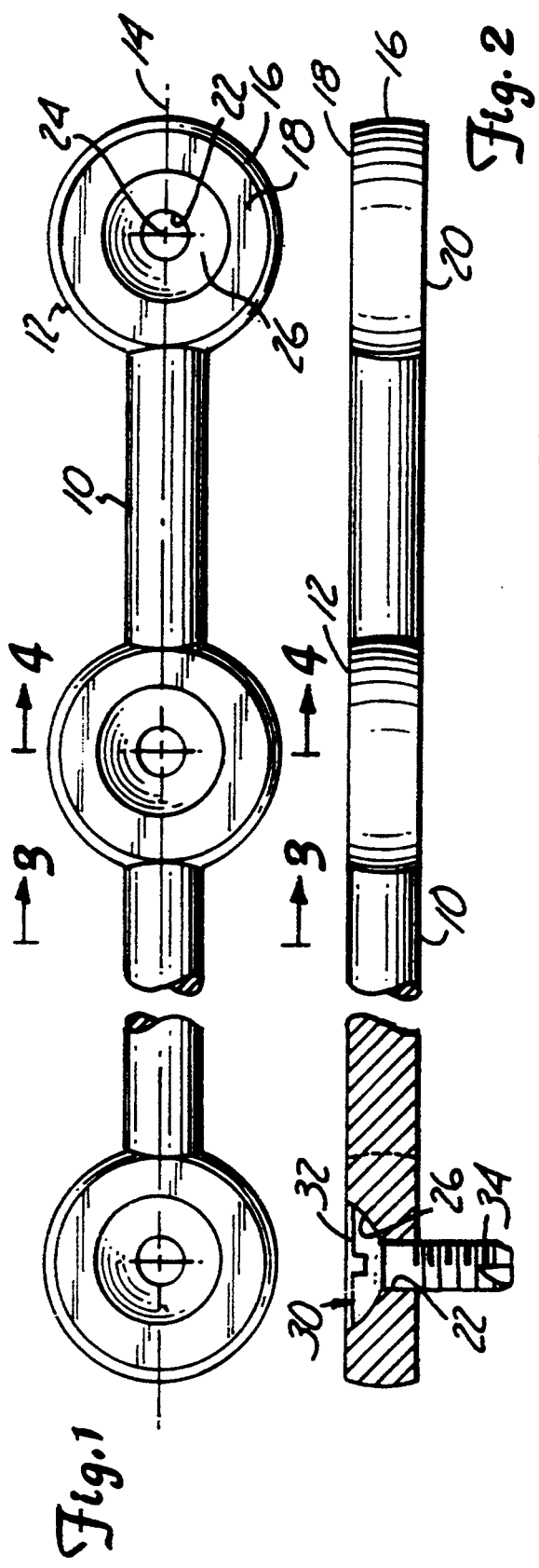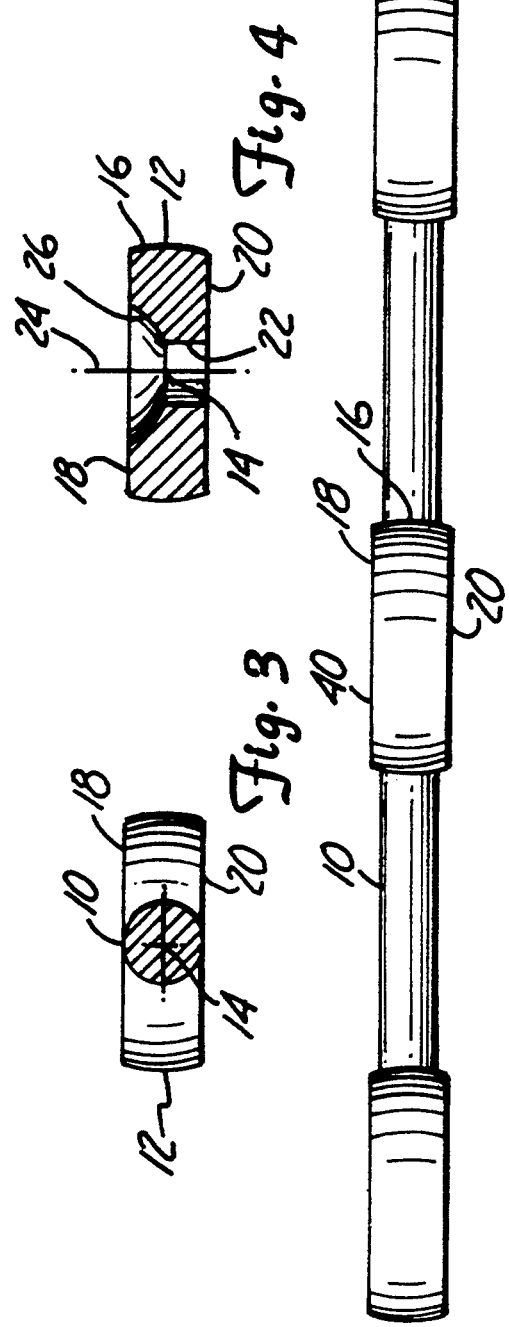

BONE FIXATION PLATE

BACKGROUND OF THE INVENTION

This invention relates to bone fixation plates, and particularly to internal or implantable fixation plates suited for stabilization of pelvic bones.

Internal or implantable bone plates are well known for stabilization of bone fractures. Most bone plates are elongated plates which include at least one flat and usually straight surface forming a bearing surface for bearing against the bone fragments to be stabilized. Some plates are curved or concave to conform to the curvature of the bone structure, and some bone plates have more than one elongated section, such as plates having "Y" shapes. Most bone plates include apertures for receiving pins or bone screws whose heads bear against the plate to affix the plate to the bone fragments to be stabilized. The plates also come in a wide variety of lengths and have a varying number of bone screw apertures. Examples of such bone plates may be found in U.S. Pat. No 2,441,765 to Hopkins, U.S. Pat. No. 3,593,709 to Halloran, U.S. Pat. No. 4,219,015 to Steinemann and U.S. Pat. No. 4,573,458 to Lower.

Pelvic bones tend to vary in size and shade between patients, thereby making it difficult to produce a single bone plate universal to all patients. Consequently, it is necessary to adapt bone plates to the specific requirements of patients by bending or twisting the plate to fit the contour or configuration of the patient's bone. Therefore, one important feature of most bone plates is that the plate must be capable of being bent to conform to the specific contour of the bone to which is to be attached. Most bone plates are designed to permit up to 15° bending or twisting. However, bone plates are most likely to break or fail at the region of the bone screw aperture where the cross-section of the material is reduced and the plate has lower tensile strength. Stress across a screw aperture on a flat plate tends to be increased by a concentration factor of nearly two. Consequently, care must be taken to avoid twisting or bending a plate at a screw aperture.

Another factor in bone plates is that the plate should have a bending resistance matched to the bone to be stabilized. If the plate is too flexible, the region of the fracture is not sufficiently stabilized, resulting in inadequate restoration. conversely, if the bone plate is too stiff, the plate takes up most of the loading forces which leads to general decay of the bone. However, the bending resistance of a bone plate is altered by forces (including friction) at the interface between the bearing surface of the bone plate and the bone surface, as well as by forces transmitted between them.

One pelvic bone plate, which is commercially available from Zimmer, Inc. as product number 1179-00, employs an elongated elliptical rod having support tabs spaced laterally along the length, the tabs having bone screw apertures for mounting the plate to the bone. This product, which is shown and described in conjunction with FIG. 6 of the aforementioned Lower patent, employs tabs which are significantly thinner than the thickness of the elongated rod portion. According to the Lower patent, the elliptical design reduces stress in the bone plate caused by twisting or bending the plate. Moreover according to Lower, the placement of the screw apertures on the lateral tabs (off the plate axis) permits distribution of stress along the length of the plate as the plate is twisted or bent.

One problem with the Lower/Zimmer design is that the laterally offset screw fasteners fastening the plate to the bone creates a bending moment in the tab which tends to concentrate stress at the intersection of the tabs and rod. Since the tabs are relatively thin, the risk exists that the tabs may sever at the junction between the tabs and the rod. Moreover, the underside of the rod portion is relatively flat and coplanar with the lower surfaces of the tab portions to form a continuous bone bearing surface along the length of the rod which encompasses the tabs. The flat bearing surface alters the intended distribution of stress caused by bending and twisting, thereby causing uneven stress distribution. Hence, stress is actually concentrated at the intersection of the tabs and rod, thereby leading to failure of the plate.

SUMMARY OF THE INVENTION

An implantable bone plate according to the present invention comprises a solid, elongated, generally circular rod member having a plurality of axially-aligned flat members spaced apart along the length thereof. Each of the flat members has a width greater than the thickness of the rod member and includes a screw aperture being normal to and intersecting the axis of the rod member.

Preferably, the flat members have a thickness at least as great as the thickness of the rod member so that only the flat members form bearing surfaces for bearing against a bone.

Also preferably, the flat members are truncated spherical members whose spherical surfaces intersect the rod member.

BRIEF DESCRIPTION OF THE DRAWINGS

FIG. 1 is a top view of the bone plate in accordance with the presently preferred embodiment of the present invention.

FIG. 2 is a side view of the bone plate, partly in cutaway cross-section.

FIGS. 3 and 4 are section views taken at lines 3—3 and 4—4, respectively, in FIG. 1.

FIG. 5 is a side view of a bone plate in accordance with a modification of the present invention.

DETAILED DESCRIPTION OF THE PREFERRED EMBODIMENTS

Figure 6:
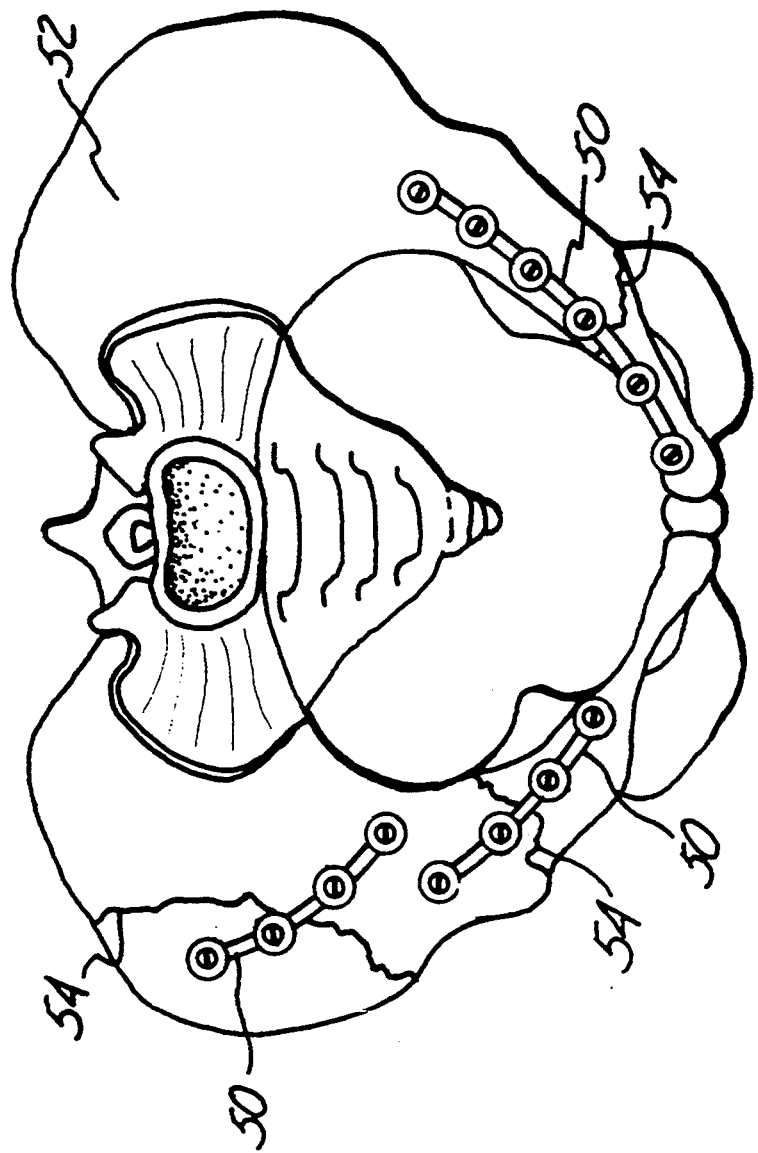
FIG. 6 illustrates a human pelvic bone structure having several bone plates of the present invention affixed across various fracture sites.

FIGS. 1 to 4 illustrate a bone plate in accordance with the presently preferred embodiment of the present invention. The bone plate comprises a solid elongated cylindrical rod member 10 having a sized diameter and a circular cross-section about axis 14. A plurality of spaced apart truncated spherical members 12 are centered along axis 14 integral to rod member 10. Each member 12 has a spherical outer surface 16 and opposing parallel flat surfaces 18 and 20 equidistant and parallel to axis 14, the flat surfaces 18 and 20 defining the thickness of the members 12. The flat surfaces are circular due to the junction with spherical outer surface 16. The thickness of each member 12 is preferably at least as great as the diameter of rod 10, and, as will be explained in connection with FIG. 5, may be greater than the diameter of rod 10.

A screw aperture 22, having a diameter sized to receive the shank of a bone screw, bone pin, or the like, extends through each member 12 between surfaces 18 and 20. Axis 24 of aperture 22 is normal to surfaces 18 and 20 and is normal to and intersects axis 14 of rod 10. An enlarged counterbore 26, coaxial with aperture 22, is formed into surface 18 and configured to receive and mate with the head of a bone screw received in aperture 22.

As shown particularly in FIG. 2, bone screw 30 has a head 32 arranged to mate with and bear against the surface of counterbore 26. Preferably, counterbore 26 is sufficiently deep into member 12 that the entire head 32 of bone screw 30 is received within the counterbore region and no portion of the head protrudes above surface 18 of the plate. The shank 34 of bone screw 30 extends through aperture 22, past surface 20 of member 12, and into the bone (not shown).

In one form of the present invention, the diameter of rod member 10 and thickness of flat members 12 is of the order of between 0.140 and 0.182 inches and the diameter of members 12 formed by spherical surfaces 16 is of the order of between 0.375 and 0.4375 inches. Thus, the diameter of members 12 is of the order of two to three times the diameter of rod member 10. The present invention employs a circular elongated rod 10 with members 12 being significantly larger to permit bending and twisting of the rod with good characteristics of stress distribution along the rod. More particularly, by providing a thickness to members 12 at least as great as the diameter of the rod, and a width to members 12 significantly greater than the diameter of the rod, bending and twisting of the rod is confined to the circular sections.

Moreover, it is known that stress concentration across an aperture is approximately twice that of a flat plate. By providing members 12 with an adequate thickness (at least as great as the diameter of rod member 10), any stress concentration across the screw apertures is adequately supported by the members 12. Preferably, members 12 are sufficiently thick so that counterbores 26 may be deep enough to entirely receive the head 32 of bone screws 30, so no sharp edge of the bone screws protrude above surface 18.

The plate according to the present invention is compressed against the bone at the location of surfaces 20 of members 12, surfaces 20 forming the bearing surface for bearing against the bone. Since the rod member 10 is circular and the bone is flat or circular in an opposite sense, any contact between the rod section and the bone is confined to the tangential line between the curved rod and the bone. As a result, and bearing of the rod portions against the bone is minimized or eliminated, and the rod member does not bear against the bone to interfere with the natural bending resistance of the bone.

One feature of the invention resides in the spherical outer shape to members 12. The spherical shape provides a significant advantage over a cylindrical or even a rectangular shape. More particularly, if members 12 were rectangular, the junction between a flat surface of a rectangular member and the circular cross-section of a cylindrical rod member would result in a transition between a circle and a flat surface. As a result, stress would be concentrated at that function, resulting in the risk of failure of the plate. If members 12 were cylindrical so that the cylindrical rod joined to the convex surface or the member, the transition would have the appearance of a partial cylinder which again would concentrate stress at the junction (although not as severely as in the rectangular example). The spherical surface of members 12, however, provides a junction which includes a portion of the length of the rod, resembling a "ball and socket" junction, thereby distributing stress more evenly, resulting in a more reliable bone plate capable of withstanding stress and permitting bending of the bone plate along the rod section.

As described above, it is preferred that the bearing surfaces of the bone plate be confined only to the region of the aperture support members 12. FIG. 5 illustrates a modified bone plate according to the present invention having a cylindrical rod 10 and spherical members 40 having screw apertures as described in connection with the invention shown in FIGS. 1–4. In the case of FIG. 5, members 40 are thicker than the diameter of rod 10 so that the opposing flat surfaces 18 and 20 define a bone screw supporting member having increased strength. Importantly, the embodiment shown in FIG. 5 assures that rod 10 is spaced from the bone being stabilized and is prevented from bearing against the bone. Thus, only members 40 bear against the bone.

FIG. 6 illustrates the manner that the bone plate according to the present invention is utilized to stabilize a fractured pelvic bone. As shown in FIG. 6, the bone plates 50 are secured to the pelvic bone structure 52 across the various fractures 54. The bone plate 50 may be twisted and bent to fit the particular contour of the pelvic bone during the fixation procedure. Bone screws are placed in screw apertures selected by the surgeon, with the common arrangement being at least two bone screws attaching the plate to the bone on each side of the fracture.

The present invention thus provides an improved bone plate capable of being bent and twisted without undue stress concentration. The plate employs axially aligned bone screw apertures to transmit stress and force along the bone plate length, without concentrating stress to cause possible failure of the bone plate.

Although the present invention has been described with reference to preferred embodiments, workers skilled in the art will recognize that changes may be made in form and detail without departing from the spirit and scope of the invention.

What is claimed is:

1. An implantable bone plate comprising a solid rod member having a length defining a longitudinal axis, the rod member having a plurality of enlarged bone-engaging members spaced apart along the length of the rod member, cylindrical portions between the bone-engaging members, the cylindrical portions having an essentially circular cross-section defining a first thickness to the rod member, the bone-engaging members and the cylindrical portions being centered on the longitudinal axis, each of the bone-engaging members having a first surface defining a bearing surface for bearing against a bone and having a second surface opposite the first surface, the first and second surfaces defining a second thickness not smaller than the first thickness, the bone-engaging members each having an aperture therein for receiving a bone fastener, each aperture having an aperture axis normal to the bearing surface and intersecting the longitudinal axis of the rod member.

2. An implantable bone plate as in claim 1 wherein the second thickness is greater than the first thickness and the bone-engaging members and cylindrical portions are arranged with respect to the rod member so that the cylindrical portions do not bear against the bone.

3. An implantable bone plate as in claim 1 wherein each aperture comprises a first bore portion arranged to receive a shank of a bone fastener and a counterbore portion arranged to receive a head of the bone fastener.

4. An implantable bone plate as in claim 3 wherein the counterbore portion has a depth in the bone-engaging member arranged to receive the entire head of the bone fastener.

5. An implantable bone plate as in claim 1 wherein each bone-engaging member has a frusto-spherical outer surface between the first and second surfaces, the cylindrical portions intersecting the bone-engaging members at the frusto-spherical surface.

6. An implantable bone plate as in claim 5 wherein each aperture comprises a first bore portion arranged to receive a shank of a bone fastener and a counterbore portion arranged to receive a head of the bone fastener.

7. An implantable bone plate as in claim 6 wherein the counterbore portion has a depth in the bone-engaging member arranged to receive the entire head of the bone fastener.

8. An implantable bone plate as in claim 5 wherein the second thickness is greater than the first thickness and the bone-engaging members and cylindrical portions are arranged with respect to the rod member so that the cylindrical portions do not bear against the bone.

9. An implantable bone plate as in claim 8 wherein each aperture comprises a first bore portion arranged to receive a shank of a bone fastener and a counterbore portion arranged to receive a head of the bone fastener.

10. An implantable bone plate as in claim 9 wherein the counterbore portion has a depth in the bone-engaging member arranged to receive the entire head of the bone fastener.

11. An implantable bone plate as in claim 1 wherein the first surface is flat.

12. An implantable bone plate comprising:
   (a) a solid rod member having a length defining a longitudinal axis and an essentially cylindrical portion defining a sized diameter;
   (b) a plurality of screw-aperture members spaced apart by the cylindrical portion along the length of the rod member and centered on the longitudinal axis, each of the screw-aperture members having
     (i) first and second surfaces arranged substantially parallel to each other and spaced apart by a distance at least as great as the diameter, the first surface defining a bearing surface for bearing against a bone,
     (ii) a frusto-spherical outer surface between the first and second surfaces, the frusto-spherical surface forming generally circular outer edges to the respective first and second surfaces, the cylindrical portion joining the frusto-spherical surface so that the first and second surfaces are each substantially parallel to the axis of the rod member, and
     (iii) an aperture extending between the first and second surfaces, the aperture having an axis substantially normal to the longitudinal axis of the rod member and arranged to receive a bone fastener.

13. An implantable bone plate as in claim 12 wherein the first and second surfaces are spaced apart by a distance greater than the diameter of the cylindrical portion so that the cylindrical portion does not bear against the bone.

14. An implantable bone plate as in claim 13 wherein each aperture comprises a first bore portion arranged to receive a shank of the bone fastener and a counterbore portion arranged to receive a head of the bone fastener.

15. An implantable bone plate as in claim 14 wherein the counterbore portion has a depth in the screw-aperture member arranged to receive the entire head of the bone fastener.

16. An implantable bone plate as in claim 12 wherein each aperture comprises a first bore portion arranged to receive a shank of a bone fastener and a counterbore portion arranged to receive a head of the bone fastener.

17. An implantable bone plate as in claim 16 wherein the counterbore portion has a depth in the screw-aperture member arranged to receive the entire head of the bone fastener.

18. An implantable bone plate as in claim 12 wherein the first surface is flat.

* * * * *

UNITED STATES PATENT AND TRADEMARK OFFICE
CERTIFICATE OF CORRECTION

PATENT NO. : 5,336,224
DATED : August 9, 1994
INVENTOR(S) : COREY M. SELMAN

It is certified that error appears in the above-indentified patent and that said Letters Patent is hereby corrected as shown below:

Col. 1, line 26, delete "shade", insert --shape--

Col. 3, line 62, delete "function", insert --junction--

Signed and Sealed this

Seventh Day of March, 1995

Attest:

BRUCE LEHMAN

Attesting Officer     Commissioner of Patents and Trademarks